United States Patent [19]

Wall et al.

[11] 3,996,248
[45] Dec. 7, 1976

[54] PREPARATION OF 2,5-DIHYDROFURANS FROM BUTADIENE MONOXIDES

[75] Inventors: Robert G. Wall, Pinole; Victor P. Kurkov, San Rafael, both of Calif.

[73] Assignee: Chevron Research Company, San Francisco, Calif.

[22] Filed: Nov. 17, 1975

[21] Appl. No.: 632,555

[52] U.S. Cl. .................................... 260/346.1 R
[51] Int. Cl.² .................................. C07D 307/28
[58] Field of Search .......................... 260/346.1 R

[56] References Cited
UNITED STATES PATENTS

| 3,812,158 | 5/1974 | Besozzi et al. | 260/346.1 R |
| 3,932,468 | 1/1976 | Kurkov | 260/346.1 R |

OTHER PUBLICATIONS

Heap et al., J. of Chem. Society (C), 1969, pp. 160–164.

*Primary Examiner*—Henry R. Jiles
*Assistant Examiner*—Bernard Dentz
*Attorney, Agent, or Firm*—G. F. Magdeburger; John Stoner, Jr.; W. Keith Turner

[57] ABSTRACT

A process for preparing a substituted or unsubstituted dihydrofuran from a substituted or unsubstituted butadiene monoxide which comprises contacting the butadiene monoxide with a catalyst comprising a hydrogen halide selected from the group consisting of hydrogen iodide or bromide and a Lewis acid.

7 Claims, No Drawings

PREPARATION OF 2,5-DIHYDROFURANS FROM BUTADIENE MONOXIDES

BACKGROUND OF THE INVENTION

The present invention relates to preparation of 2,5-dihydrofuran from butadiene monoxide. The dihydrofuran can be hydrogenated to tetrahydrofuran, which is a good solvent for high-molecular-weight polyvinyl chloride, polyvinylidene chloride, and other difficulty soluble organic materials.

Closely related compounds can be prepared from 2,5-dihydrofuran. 2,3-dihydrofuran can be obtained by isomerizing 2,5-dihydrofuran (see, for example, U.S. Pat. No. 2,556,325); and tetrahydrofuran is readily produced from a dihydrofuran by hydrogenation.

Prior methods for preparation of tetrahydrofuran include catalytic hydrogenation of furan, which, in turn, can be prepared by decarbonylation of furfural (see, for example, U.S. Pat. No. 2,374,149 and 2,846,449). Furfural in the past has been produced from naturally occurring vegetable materials such as corn cobs and oat hulls.

In addition to obtaining tetrahydrofuran from furfural as a source material, tetrahydrofuran can also be produced by heating 1,4-butylene glycol — for example, in an overall process using acetylene as the starting material and having the following steps:

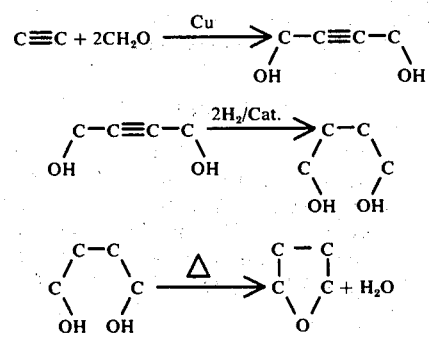

Relating to the production of tetrahydrofuran from 1,4-butylene glycol by heating under specified conditions, see the disclosures of, for example, Reppe et al. U.S. Pat. Nos. 2,251,292, 2,251,835, and 2,251,895; and also Rogers U.S. Pat. No. 3,467,679.

Production of tetrahydrofuran by hydrogenation of maleic anhydride is described by T. Yoshimura in "Chemical Engineering", 1969, at page 70.

Oxidation of 1,3-butadiene to furan using a catalyst such as manganese molybdate is disclosed in U.S. Pat. No. 2,900,396. Oxidation of various organic compounds to furan using a bismuth-molybdenum catalyst at a temperature of at least 350° C is disclosed in U.S. Pat. No. 3,600,405. Crotonaldehyde (propylene aldehyde) is a preferred feedstock in the process of U.S. Pat. No. 3,600,405; other feedstocks disclosed are acetals and hemi-acetals of crotonaldehyde, aldol, butadiene monoxide, crotyl alcohol, n-butyl alcohol, 1,4-butanediol and n-butyraldehyde.

The present invention is particularly concerned with preparation of dihydrofuran from an epoxide by rearrangement. An example of an epoxide rearrangement is disclosed by Heap et al. in the "Journal of the Chemical Society", 1969, at page 160. Heap et al reported that 1,3-cyclooctadiene oxide was rearranged in the presence of perchloric acid to 9-oxabicyclo(4,2,1)non-7-ene in about 50% yield:

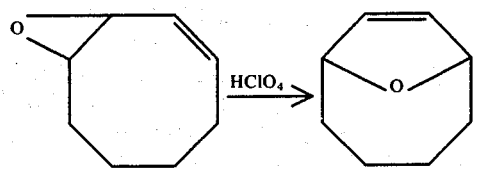

SUMMARY OF THE INVENTION

According to the present invention a process is provided for preparing a substituted or unsubstituted dihydrofuran from a substituted or unsubstituted butadiene monoxide, which process comprises contacting the butadiene monoxide with a catalyst comprising a hydrogen halide selected from the group consisting of hydrogen iodide or bromide and a select Lewis acid comprising a metal selected from the group consisting of zinc, aluminum, boron, magnesium, and tin in an organic solvent under conditions effective to convert the butadiene monoxide to the dihydrofuran and wherein said Lewis acid is effective to accelerate said conversion.

Among other factors, the present invention is based on my discovery that butadiene monoxide can be converted to 2,5-dihydrofuran using hydrogen iodide or hydrogen bromide and certain effective metal catalysts and that unexpectedly high yields of 2,5-dihydrofuran are achieved in such process.

Preferably the process of the present invention is used to produce 2,5-dihydrofuran which does not have substituents attached thereto, i.e. unsubstituted dihydrofurans. However, substituted dihydrofurans can also be produced by the method of the present invention. The terminology "substituted dihydrofurans" or "substituted butadiene monoxide" is used to connote that the basic dihydrofuran or butadiene monoxide structure has a substitutent attached onto it as, for example, an alkyl group attached onto the basic dihydrofuran or butadiene monoxide structure. For instance, 1,2-epoxy-2-methyl-3-butene and 1,2-epoxy-3-methyl-3-butene can be converted to 3-methyl-2,5-dihydrofuran using an aluminum metal catalyst and hydrogen iodide. Preferred substituted butadiene monoxide feedstocks for producing substituted dihydrofuran are substituted butadienes having one or more alkyl groups containing 1-8 carbon atoms which could also be part of a ring, such as 1,3-pentadiene, 1,3-hexadiene, 2,3-dimethyl-1,3-pentadiene, 1,3-octadiene, cyclopentadiene, 1,3-cyclooctadiene, 1,3-cyclododecatriene, etc; substituted butadienes having one or more halogens, such as chloroprene, 2,3-dichlorobutadiene, 1,4-dichlorobutadiene, 1,1-dichlorobutadiene, and bromoprene.

Preferably the reaction is carried out in liquid phase using an organic solvent such as N-methyl-pyrrolidone. Suitable organic solvents for the present invention are inert organic media such as substituted amides, hydrocarbons and chlorinated hydrocarbons, i.e., N-methylpyrrolidone, benzene, xylenes, hexane, chlorobenzene, etc.

It has been found that certain amines will react in the reaction system of the present invention — these amines are not suitable for the process of the present invention. Such amines in particular include N-methylpyrrolidine and 2,6-dimethylpiperidine. These latter-type organic compounds are believed to react with iodo- or bromohydrin compounds in the reaction system — in particular they are believed to be alkylated by the halohydrin compound.

Thus, preferably the inert organic solvent used in the present invention is a solvent which is not readily alkylated under the reaction conditions of the present process. Tertiary amides, i.e., amides which have both the hydrogen groups substituted by organic radicals, are especially preferred inert organic media. Particularly preferred tertiary amides for use herein are N-methylpyrrolidone, N,N-dimethylformamide, N,N-dimethylacetamide, etc.

The metallic catalyst used in the present invention is a homogeneous catalyst, as opposed to a heterogeneous catalyst, and thus the metal should be coordinated with suitable ligands to solubilize the metal in the organic reaction medium. For example, aluminum having a valence of +3 [aluminum(III)] coordinated with acetylacetone was found to be especially effective. In this case the aluminum (III) is, of course, coordinated with three organic ligands. In general, the ligand coordinated with the metal can be substantially any organic or inorganic ligand which will solubilize the metal in the organic reaction medium.

Preferred Lewis acid catalysts are those wherein the metal is aluminum, zinc or magnesium. Of these metals, aluminum has been found to give the highest yields. The preferred amount of catalyst varies from 0.01 to 0.3, preferably 0.02 to 0.1, mols per mol of butadiene monoxide.

Preferably the hydrogen halide used in the present invention is hydrogen iodide. Preferred molar ratios of the hydrogen halide to butadiene monoxide are 0.01 to 1:1, and especially preferred ratios are 0.03 to 0.3:1.

Preferred reaction temperatures for the process of the present invention are between 50° and 140° C, and especially preferred temperatures are between 80° and 120° C. The reaction is normally carried out in liquid phase and thus a pressure is usually maintained sufficient to retain liquid phase. Usually the pressure is between about 1 atmosphere and 60 atmospheres, and preferably between about 1 and 30 atmospheres.

EXAMPLES

EXAMPLE 1

500 millimols (mmols) N-methylpyrrolidone (NMP), 6 mmols of potassium iodide (KI), 6 mmols of hydrogen iodide (HI), 200 mmols of butadiene monoxide (BDMO) and 6 mmols of aluminum acetylacetonate (Al[AcAc]$_3$) were placed in a glass pressure vessel provided with a thermometer, magnetic stirrer and sample tube. The flask was pressurized with nitrogen and vented to flush out air. The reactants were heated at 240°–246° F by immersion of a preheated oil bath for 1 hour. Vapor phase chromatograph (VPC) analysis showed 84% yield of 2,5-dihydrofuran.

In the above procedure an equivalent amount of hydrogen bromide and hydrogen chloride is substituted for HI and similar results are achieved.

In the above procedure an equivalent amount of N-methylpyrrolidone/benzene (1:1), N-methylpyrrolidone/benzene (1:2), and N,N-dimethylformamide, respectively, is substituted for N-methylpyrrolidone and substantially equivalent results are achieved.

In the above procedure an equivalent amount of isoprene oxides, 4.4: 1 mixture of 3,4-epoxy-3-methyl-1-butene and 3,4-epoxy-2-methyl-1-butene is substituted for butadiene monoxide and 3-methyl-2,5-dihydrofuran is obtained.

EXAMPLE 2

Using the procedure of Example 1, 5 mmols of magnesium acetylacetonate (Mg[AcAc]$_2$) and 15 mmols of HI were used to catalyze the conversion of 200 mmols of butadiene monoxide dissolved in 500 mmols of N-methylpyrrolidone. The reaction mixture was heated at about 270° F for 15 minutes. The yield of 2,5-dihydrofuran obtained was 41%.

EXAMPLE 3

Using the procedure of Example 1, 5 mmols of zinc chloride (ZnCl$_2$), 6 mmols of HI and 6 mmols of KI were used to catalyze the conversion of 200 mmols of butadiene monoxide dissolved in 500 mmols of N-methylpyrrolidone. The reaction mixture was heated at about 240° F under reflux for about 20 minutes. The yield of 2,5-dihydrofuran was 58%.

EXAMPLE 4

Using the procedure of Example 1, 5 mmols of stannous chloride (SnCl$_2$), 6 mmol of KI and 6 mmols of HI were used to catalyze the conversion of 200 mmols of butadiene monoxide dissolved in 500 mmols of N-methylpyrrolidone. The reaction mixture was heated at about 270° F for 15 minutes. The yield of 2,5-dihydrofuran was 34%.

EXAMPLE 5

Using the procedure of Example 1, 5 mmols of stannic chloride (SnCl$_4$) and 6 mmol of HI were used to catalyze the conversion of 200 mmols of butadiene monoxide dissolved in 500 mmols of N-methylpyrrolidone. The reaction mixture was heated at about 240°–315° F for 10 minutes. The yield of 2,5-dihydrofuran was 31%.

EXAMPLE 6

Using the procedure of Example 5, 4.4 mmols of SnCl$_4$ and 6.5 mmols of KI were used to catalyze the conversion of 200 mmols of butadiene monoxide dissolved in 500 mmols of N-methylpyrrolidone. The reaction mixture was heated at about 200° F for about 1.3 hours. The yield of 2,5-dihydrofuran was 21%.

What is claimed is:

1. A process for preparing a substituted or unsubstituted 2,5 dihydrofuran from a substituted or unsubstituted butadiene monoxide which comprises contacting the butadiene monoxide with a catalyst comprising a hydrogen halide selected from the group consisting of hydrogen iodide or bromide and a homogeneous metal compound in an inert organic solvent under liquid phase reaction conditions effective to convert the butadiene monoxide to the dihydrofuran, said reaction conditions including a temperature between 50° and 140° C, and wherein said metal is zinc, aluminum, boron, tin, or magnesium, and wherein the metal is coordinated with suitable organic or inorganic ligands to solubilize the metal in the organic solvent.

2. A process in accordance with claim 1 wherein the metal is aluminum (III).

3. A process in accordance with claim 2 wherein the hydrogen halide is hydrogen iodide.

4. A process in accordance with claim 1 wherein the organic solvent is an inert solvent which is substantially unalkylated under the reaction conditions.

5. A process in accordance with claim 4 wherein the solvent comprises a tertiary organic amide.

6. A process in accordance with claim 5 wherein the solvent is N-methylpyrrolidone or N,N-dimethylformamide or N,N-dimethylacetamide.

7. A process in accordance with claim 3 wherein the solvent is N-methylpyrrolidone or N,N-dimethylformamide or N,N-dimethylacetamide.

* * * * *